US010894062B2

(12) United States Patent
Chang

(10) Patent No.: US 10,894,062 B2
(45) Date of Patent: Jan. 19, 2021

(54) VITAMIN SUPPLEMENT COMPOSITIONS FOR INJECTION

(71) Applicant: Aquavit Pharmaceuticals, Inc., New York, NY (US)

(72) Inventor: Sobin Chang, New York, NY (US)

(73) Assignee: AQUAVIT PHARMACEUTICALS, INC., New York, NY (US)

( * ) Notice: Subject to any disclaimer, the term of this patent is extended or adjusted under 35 U.S.C. 154(b) by 882 days.

(21) Appl. No.: 14/420,856

(22) PCT Filed: Aug. 9, 2013

(86) PCT No.: PCT/US2013/054421
§ 371 (c)(1),
(2) Date: Feb. 10, 2015

(87) PCT Pub. No.: WO2014/026161
PCT Pub. Date: Feb. 13, 2014

(65) Prior Publication Data
US 2015/0238527 A1 Aug. 27, 2015

Related U.S. Application Data

(60) Provisional application No. 61/682,056, filed on Aug. 10, 2012, provisional application No. 61/862,024, filed on Aug. 4, 2013, provisional application No. 61/862,026, filed on Aug. 4, 2013, provisional application No. 61/862,027, filed on Aug. 4, 2013.

(51) Int. Cl.
| | |
|---|---|
| *A61K 35/16* | (2015.01) |
| *A61K 8/27* | (2006.01) |
| *A61K 8/41* | (2006.01) |
| *A61K 8/67* | (2006.01) |
| *A61K 9/00* | (2006.01) |
| *A61K 31/137* | (2006.01) |
| *A61K 31/197* | (2006.01) |
| *A61K 31/315* | (2006.01) |
| *A61K 31/375* | (2006.01) |
| *A61K 31/4415* | (2006.01) |
| *A61K 31/445* | (2006.01) |
| *A61K 31/51* | (2006.01) |
| *A61K 31/525* | (2006.01) |
| *A61K 31/714* | (2006.01) |
| *A61K 31/715* | (2006.01) |
| *A61K 31/728* | (2006.01) |
| *A61K 33/30* | (2006.01) |
| *A61M 5/30* | (2006.01) |
| *A61M 37/00* | (2006.01) |
| *A61Q 7/00* | (2006.01) |
| *A61Q 19/08* | (2006.01) |
| *A61K 31/455* | (2006.01) |
| *A61Q 19/00* | (2006.01) |

(52) U.S. Cl.
CPC .............. *A61K 35/16* (2013.01); *A61K 8/27* (2013.01); *A61K 8/41* (2013.01); *A61K 8/673* (2013.01); *A61K 8/675* (2013.01); *A61K 8/676* (2013.01); *A61K 9/0019* (2013.01); *A61K 31/137* (2013.01); *A61K 31/197* (2013.01); *A61K 31/315* (2013.01); *A61K 31/375* (2013.01); *A61K 31/4415* (2013.01); *A61K 31/455* (2013.01); *A61K 31/51* (2013.01); *A61K 31/525* (2013.01); *A61K 31/714* (2013.01); *A61K 31/715* (2013.01); *A61K 31/728* (2013.01); *A61K 33/30* (2013.01); *A61M 5/30* (2013.01); *A61M 37/0015* (2013.01); *A61Q 7/00* (2013.01); *A61Q 19/00* (2013.01); *A61Q 19/08* (2013.01); *A61K 2800/10* (2013.01); *A61K 2800/5922* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 7,879,341 B2 | 2/2011 | Taylor | |
| 9,622,957 B2 | 4/2017 | Tezel | |
| 9,795,774 B2 | 10/2017 | Takada | |
| 9,993,423 B2 | 6/2018 | Quan | |
| 2006/0018867 A1 | 1/2006 | Kawasaki | |
| 2007/0142855 A1 | 6/2007 | Hantash | |
| 2007/0142885 A1 | 6/2007 | Hantash | |
| 2007/0178121 A1 | 8/2007 | First | |
| 2008/0161782 A1 | 7/2008 | Chan et al. | |
| 2010/0068232 A1 | 3/2010 | Key | |
| 2010/0196445 A1 | 8/2010 | David et al. | |
| 2013/0078228 A1* | 3/2013 | Abiko .................. | A61K 9/0019 424/94.1 |

FOREIGN PATENT DOCUMENTS

| | | | |
|---|---|---|---|
| WO | WO-0126642 A2 | 4/2001 | |
| WO | WO 2008/072229 A2 | 6/2008 | |

(Continued)

OTHER PUBLICATIONS

Sivagnanam, G., Mesotherapy—The French connection, 2010, J Pharmacol Pharmacother, 1(1), pp. 4-8 (Year: 2010).*

(Continued)

*Primary Examiner* — Kortney L. Klinkel
*Assistant Examiner* — Tori Strong
(74) *Attorney, Agent, or Firm* — Nevrivy Patent Law Group P.L.L.C.

(57) ABSTRACT

The embodiments relate to improved vitamin supplement compositions formulated for administration to patients, particularly improved vitamin compositions formulated for use in cosmetic or therapeutic applications. The compositions may be used to slow aging process and promote wellness including treating a vitamin deficiency, skin conditions, improving skin appearance, wound healing and scar prevention and hair loss.

17 Claims, No Drawings

(56) References Cited

FOREIGN PATENT DOCUMENTS

| WO | WO-2010097564 A2 * | 9/2010 | ............... A61K 8/06 |
|---|---|---|---|
| WO | WO 2011/138973 A1 | 11/2011 | |
| WO | WO-2011138971 A1 | 11/2011 | |
| WO | WO-2014026161 A1 | 2/2014 | |

OTHER PUBLICATIONS

International Search Report dated Feb. 10, 2015, regarding PCT/US2014/049652.

International Search Report dated Nov. 4, 2013, regarding PCT/US2013/054421.

Borrione et al. Platelet-rich plasma in muscle healing. Am J Phys Med Rehabil. 89(10): 854-61. (2010).

Fagien et al. Reconstituted injectable hyaluronic acid: expanded application in facial aesthetics and additional thoughts on the mechanism of action in cosmetic medicine. Plastic and reconstructive surgery 130: 208-217 (2012).

Molnar. Nutrition and Wound Healing. CRC Press Chapter 7,8,10 (2006).

Olsen et al. A multicenter, randomized, placebo-controlled, double-blind clinical trial of a novel formulation of 5% minoxidil topical foam versus placebo in the treatment of androgenetic alopecia in men. J Am Acad Dermatol 57(5): 767-74 (2007).

Papakonstantinou et al. Hyaluronic acid: A key molecule in skin aging. Dermato-endocrinology 4: 253-258 (2012).

Sculptra Aesthetic (injectable poly-L-lactic acid) Bridgewater, NJ. Sanofi-Aventis U.S. LLC. (2012).

Varani et al. Decreased Collagen Production in Chronically Aged Skin. Am J Pathol. 168(6): 1861-1868 (2006).

* cited by examiner

VITAMIN SUPPLEMENT COMPOSITIONS FOR INJECTION

CROSS-REFERENCE

This application is a § 371 national stage application of International PCT Application No. PCT/US2013/054421, which is a claims the benefit of U.S. Provisional Application No. 61/682,056, filed Aug. 10, 2012, entitled "VITAMIN SUPPLEMENT COMPOSITIONS FOR INTRAMUSCULAR INJECTION"; U.S. Provisional Application No. 61/862,024, filed Aug. 4, 2013, entitled "BIOACTIVE FORMULATIONS FOR AESTHETIC ENHANCEMENT"; U.S. Provisional Application No. 61/862,026, filed Aug. 4, 2013, entitled "IMPROVING SKIN HEALTH USING MICRONEEDLE DELIVERY OF BIOACTIVE FORMULATIONS"; and U.S. Provisional Application No. 61/862,027, filed Aug. 4, 2013, entitled "MICRONEEDLE DEVICE FOR TRANSDERMAL DRUG DELIVERY"; all of which are incorporated herein by reference in their entirety.

TECHNICAL FIELD

Embodiments described herein relate to vitamin supplement compositions formulated for injection and methods of use thereof.

BACKGROUND OF THE INVENTION

Supplementing the diet with additional vitamins and minerals can be a valuable therapy for those with dietary imbalances or different nutritional needs (e.g., for disease prevention). People with dietary imbalances may include those on restrictive diets and those who cannot or will not eat a nutritious diet. Vitamin and mineral supplements are commonly administered to treat specific medical conditions or as general nutritional supplements. Nutritional supplements, often containing vitamins, are used to ensure that adequate amounts of nutrients are obtained if optimal amounts of the nutrients cannot be obtained through a varied diet.

B vitamins are a group of water-soluble vitamins that play important roles in cell metabolism. The B vitamins are B1 (thiamine), B2 (riboflavin), B3 (niacin), B5 (pantothenic acid), B6 (pyridoxine), B7 (biotin), B12 (cobalamin) and folic acid. The B vitamins play an important role in many aspects of the body's functioning, and a vitamin B deficiency can have a serious impact on overall health.

Vitamin B supplements are known in the art: such formulations are limited in terms of absorption (oral dosage forms) or may require a hospital visit (IV therapy) at significant cost in terms of time and expense.

Hyaluronic acid (HA) is widely distributed in both prokaryotic and eukaryotic cells. In humans, HA is present in all tissues, especially in the skin (Ref. 1). The biological functions of HA include hydration, lubrication of joints, filling capacity, and providing a framework for cells migration[1]. HA also involves in tissue repair, wound healing and immune responses. In terms of cosmetic and aesthetic use, HA plays a role in hydration of the skin and reducing collagen deposition, which leads to reduced scarring. HA-related products are usually used as "dermal fillers".

Due to the lack of suitability of its application with currently formulation availability, HA products are less likely used in treating facial fine lines. Instead, they are more often applied in treatment of deep facial lines (Ref. 2). The present invention describe a composition of vitamins and HA for treating facial fine lines, for both intradermal and topical use.

SUMMARY OF THE INVENTION

There exists a need for vitamin formulations. The present inventors have developed new vitamin compositions formulated for intramuscular injection which can be used to treat or ameliorate a disease or one or more symptoms associated with a vitamin deficiency or other condition in a human patient. Included in the formulations described herein are new intramuscular (IM) injectable formulations that are designed to improve skin condition and appearance, e.g., from inside, rather than topical administration of, for example, a cream agent. For example, administration of a composition provided herein may improve skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent.

There exists a need for vitamin formulations. The present inventors have developed new vitamin compositions formulated for injection which can be used to treat or ameliorate a disease or one or more symptoms associated with a vitamin deficiency or other condition in a human patient. Included in the formulations described herein are new injectable formulations that are designed to improve skin condition and appearance, e.g., from inside, rather than topical administration of, for example, a cream agent. For example, administration of a composition provided herein may improve skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent.

In one aspect, provided herein is an aqueous solution adapted for human administration, comprising: from about 1500 to about 6250 mcg cobalamin (vitamin B12); from about 150 to about 250 mg ascorbic acid (vitamin C); from about 30 to about 50 mg nicotinamide (vitamin B3); from about 4.5 to about 7.5 mg thiamine (vitamin B1); from about 0.1 to about 0.3 mg pyridoxine HCl (vitamin B6); from about 2.7 to about 4.5 mg riboflavin 5-phosphate sodium (vitamin B2); from about 7.5 to about 15 mg pantothenic acid (vitamin B5); from about 0.08 to about 0.125 mg Zinc sulfate heptahydrate; optionally a chemical stabilizer; optionally a preservative; and optionally an additional bioactive agent; wherein the aqueous solution is formulated for injection.

In one aspect, provided herein is an aqueous solution adapted for human administration, the solution comprising: 5000 mcg cobalamin (vitamin B12); 200 mg ascorbic acid (vitamin C); 40 mg nicotinamide (vitamin B3); 6 mg thiamine (vitamin B1); 0.1 mg pyridoxine HCl (vitamin B6); 3.6 mg riboflavin 5-phosphate sodium (vitamin B2); and 10 mg pantothenic acid (vitamin B5); and 0.1 mg Zinc sulfate heptahydrate.

In one embodiment, the chemical stabilizer is gentisic acid. In another embodiment, the preservative is benzyl alcohol. In another embodiment, the additional bioactive agent is hyaluronic acid, botulinum toxin, platelet-rich plasma, or polylatic acid. The solution may have a pH between about 7.2 and 7.6. In one instance, the solution has a pH of 7.4. Cobalamin to be used in the solutions may be, for example, cyanocobalamin or methylcobalamin.

Preservatives, chemical stabilizers, and/or additional bioactive agents may be added to the compositions in an amount of between about 0.01% and about 2% of the total volume. In one instance, a preservative may be added to the compositions in an amount of between about 0.01% and about 2% of the total volume. In another instance, a chemical stabilizer may be added to the compositions in an amount of between about 0.01% and about 2% of the total volume. In yet another instance, an additional bioactive agent may be added to the compositions in an amount of between about 0.01% and about 2% of the total volume. In yet another instance, two or a preservative, chemical stabilizer and an additional bioactive agent may be added to the compositions in an amount of between about 0.01% and about 2% of the total volume.

In one aspect, provided herein is an aqueous solution formulated for intramuscular injection comprising: from about 1500 to about 6250 mcg cobalamin (vitamin B12); from about 150 to about 250 mg ascorbic acid (vitamin C); from about 30 to about 50 mg nicotinamide (vitamin B3); from about 4.5 to about 7.5 mg thiamine (vitamin B1); from about 0.1 to about 0.3 mg pyridoxine HCl (vitamin B6); between about 2.7 to about 4.5 mg riboflavin 5-phosphate sodium (vitamin B2); from about 7.5 to about 15 mg pantothenic acid (vitamin B5); and from about 0.08 to about 0.125 mg Zinc sulfate heptahydrate.

In one non-limiting example, a solution may comprise: 5000 mcg cobalamin (vitamin B12); 200 mg ascorbic acid (vitamin C); 40 mg nicotinamide (vitamin B3); 6 mg thiamine hydrochloride (vitamin B1); 0.1 mg pyridoxine hydrochloride (vitamin B6); 3.6 mg riboflavin 5-phosphate sodium (vitamin B2); 10 mg pantothenic acid (vitamin B5); and 0.1 mg Zinc sulfate heptahydrate.

Preservatives, chemical stabilizers, and/or additional bioactive agents may be added to the compositions in an amount of between about 0.01% and about 2% of the total volume. In one instance, a preservative may be added to the compositions in an amount of between about 0.01% and about 2% of the total volume. In another instance, a chemical stabilizer may be added to the compositions in an amount of between about 0.01% and about 2% of the total volume. In yet another instance, an additional bioactive agent may be added to the compositions in an amount of between about 0.01% and about 2% of the total volume. In yet another instance, two or a preservative, chemical stabilizer and an additional bioactive agent may be added to the compositions in an amount of between about 0.01% and about 2% of the total volume. In one embodiment, the chemical stabilizer is gentisic acid. In another embodiment, the preservative is benzyl alcohol. In another embodiment, the additional bioactive agent is hyaluronic acid, botulinum toxin, platelet-rich plasma, or polylatic acid.

The solution may have a pH between about 7.2 and 7.6. In one instance, the solution has a pH of 7.4. Cobalamin to be used in the solutions may be, for example, cyanocobalamin or methylcobalamin.

In one aspect, provided herein is a needleless injection device or a prefilled syringe comprising any of the aqueous solutions described herein. A needleless injection device or pre-filled syringe may, in some instances, comprise: from about 1500 to about 6250 mcg cobalamin (vitamin B12); from about 150 to about 250 mg ascorbic acid (vitamin C); from about 30 to about 50 mg nicotinamide (vitamin B3); from about 4.5 to about 7.5 mg thiamine (vitamin B1); from about 0.1 to about 0.3 mg pyridoxine HCl (vitamin B6); from about 2.7 to about 4.5 mg riboflavin 5-phosphate sodium (vitamin B2); from about 7.5 to about 15 mg pantothenic acid (vitamin B5); and from about 0.08 to about 0.125 mg Zinc sulfate heptahydrate.

In one aspect, provided herein is a container comprising an aqueous solution formulated for intramuscular injection, the aqueous solution comprising: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); pantothenic acid (vitamin B5); and Zinc sulfate heptahydrate; wherein the container optionally comprises a UV-blocking agent which help prevent degradation of components of the compositions. A container may be, for example, an ampoule, a vial, a needleless injection device or a pre-filled syringe.

In one aspect, provided herein is a method of treating or ameliorating a disease or one or more symptoms of a condition in a patient in need thereof, comprising administering to the patient an aqueous solution comprising: from about 1500 to about 6250 mcg cobalamin (vitamin B12); from about 150 to about 250 mg ascorbic acid (vitamin C); from about 30 to about 50 mg nicotinamide (vitamin B3); from about 4.5 to about 7.5 mg thiamine (vitamin B1); from about 0.1 to about 0.3 mg pyridoxine HCl (vitamin B6); from about 2.7 to about 4.5 mg riboflavin 5-phosphate sodium (vitamin B2); from about 7.5 to about 15 mg pantothenic acid (vitamin B5); and from about 0.08 to about 0.125 mg Zinc sulfate heptahydrate; wherein the composition is administered to the patient through subcutaneous, intradermal, intravenous, or intramuscular administration.

One or more symptoms may be selected from depression, dementia, fibrobromyalgia, gastrointestinal disorder, headaches, chronic fatigue syndrome, high stress levels, hyperthyroidism, low energy, impaired memory, hair loss, wound healing, scarring, aging, longevity, wellness purpose, and a combination thereof.

A disease to be treated includes, but is not limited to, beriberi, Wernicke's encephalophay, ariboflavinosis, pellagra, acne, paresthesia, microcyrtic anemia, and macrocytic anemia.

In some instances, administration of said composition improves skin elasticity, skin regeneration, metabolism, or a combination.

A aqueous solution may, in some instances, consist essentially of: 5 mg cobalamin (vitamin B12); 200 mg ascorbic acid (vitamin C); 40 mg nicotinamide (vitamin B3); 6 mg thiamine (vitamin B1); 0.1 mg pyridoxine HCl (vitamin B6); 3.6 mg riboflavin 5-phosphate sodium (vitamin B2); and 10 mg pantothenic acid (vitamin B5); and 0.1 mg Zinc sulfate heptahydrate.

In one embodiment, an aqueous solution may further comprise a chemical stabilizer. In another embodiment, an aqueous solution may further comprise a preservative. In another embodiment, an aqueous solution may further comprise a chemical stabilizer and a preservative.

In one aspect, provided herein is a method of improving wound healing in a human patient in need thereof, comprising administering to the patient an aqueous solution comprising: from about 1500 to about 6250 mcg cobalamin (vitamin B12); from about 150 to about 250 mg ascorbic acid (vitamin C); from about 30 to about 50 mg nicotinamide (vitamin B3); from about 4.5 to about 7.5 mg thiamine (vitamin B1); from about 0.1 to about 0.3 mg pyridoxine HCl (vitamin B6); from about 2.7 to about 4.5 mg riboflavin 5-phosphate sodium (vitamin B2); from about 7.5 to about 15 mg pantothenic acid (vitamin B5); and from about 0.08 to about 0.125 mg Zinc sulfate heptahydrate; wherein the composition is administered to the patient through subcutaneous, intradermal, intravenous, or intramuscular administration. In one embodiment, a wound is a post-surgical wound. An aqueous solution may be administered to the patient prior to surgery. Alternatively, or in addition, an aqueous solution may be administered to the patient after surgery.

In another instance, an aqueous solution consists essentially of: 5000 mg cobalamin (vitamin B12); 200 mg ascorbic acid (vitamin C); 40 mg nicotinamide (vitamin B3); 6 mg thiamine (vitamin B1); 0.1 mg pyridoxine HCl (vitamin B6); 3.6 mg riboflavin 5-phosphate sodium (vitamin B2); 10 mg pantothenic acid (vitamin B5); and 0.1 mg Zinc sulfate heptahydrate.

In one aspect, provided herein is an aqueous solution adapted for human administration, the aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; optionally a chemical stabilizer; and optionally a preservative, wherein the aqueous solution is formulated for intramuscular injection. Preservatives and chemical stabilizers may be added, in some instances, to the compositions in an amount of between about 0.01% and about 2% of the total volume.

In one aspect, provided herein is an aqueous solution adapted for human administration, the aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); between about 0.08 to about 0.125 mg Zinc sulfate heptahydrate; optionally a chemical stabilizer; optionally a preservative; and optionally an additional bioactive agent such as hyaluronic acid, botulinum toxin, platelet rich plasma (PRP), or polylactic acid wherein the aqueous solution is formulated for injection. Preservatives, chemical stabilizers, and/or additional bioactive agents may be added to the compositions in an amount of between about 0.01% and about 2% of the total volume. In one instance, a preservative may be added to the compositions in an amount of between about 0.01% and about 2% of the total volume. In another instance, a chemical stabilizer may be added to the compositions in an amount of between about 0.01% and about 2% of the total volume. In yet another instance, an additional bioactive agent may be added to the compositions in an amount of between about 0.01% and about 2% of the total volume. In yet another instance, two or a preservative, chemical stabilizer and an additional bioactive agent may be added to the compositions in an amount of between about 0.01% and about 2% of the total volume.

In one embodiment, the product comprises an aqueous solution comprising about 1000 mcg cobalamin (vitamin B12); about 200 mg ascorbic acid (vitamin C); about 40 mg nicotinamide (vitamin B3); about 6 mg thiamine (vitamin B1); about 6 mg pyridoxine HCl (vitamin B6); about 3.6 mg riboflavin 5-phosphate sodium (vitamin B2); and about 1 mg zinc. A product provided herein may, in some instances, contain three, four, five, six, or all 7 of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); and zinc.

In one embodiment, the product comprises an aqueous solution comprising about 5000 mcg cobalamin (vitamin B12); about 200 mg ascorbic acid (vitamin C); about 40 mg nicotinamide (vitamin B3); about 6 mg thiamine (vitamin B1); about 0.25 mg pyridoxine HCl (vitamin B6); about 3.6 mg riboflavin 5-phosphate sodium (vitamin B2); 10 mg B5, and about 0.1 mg zinc. A product provided herein may, in some instances, contain three, four, five, six, seven or all eight of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); Pantothetic acid (vitamin B5) and Zinc sulfate heptahydrate.

The term "formulated for injection" refers to composition prepared for injection of a substance intravenously, intradermally, subcutaneously, intramuscularly, etc., wherein the composition is an aqueous solution consisting of water-soluble components and is prepared in a volume not to exceed 2 ml. Volumes formulated for injection include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. Injection may occur via, e.g., syringe, pre-filled syringe, needleless injector, etc.

The term "formulated for intradermal injection" refers to composition prepared for direct injection of a substance into dermis, wherein the composition is an aqueous solution consisting of water-soluble components and is prepared in a volume not to exceed 1 ml. Volumes formulated for dermal injection include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. Dermal injection may occur via, e.g., micro-needles, syringe, pre-filled syringe, needleless injector, etc.

The term "cobalamin" or "vitamin B12" encompass multiple forms of vitamin B12 suitable for human administration, including cyanocobalamin or methylcobalamin.

In one embodiment, a non-limiting example of an aqueous solution formulated for intramuscular injection comprises between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); and between about 0.5 to about 1.5 mg zinc.

In one embodiment, a non-limiting example of an aqueous solution formulated for intramuscular injection comprises between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate.

In one embodiment, a non-limiting example of an aqueous solution formulated for intramuscular injection comprises about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc.

In one embodiment, a non-limiting example of an aqueous solution formulated for intramuscular injection comprises about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); 10 mg pantothenic acid (vitamin B5); and about 0.1 mg Zinc Sulfate Heptahydrate.

In another aspect, the aqueous solution can have a pH of from about 6.0 to about 8.0. In another aspect, the aqueous solution can have a pH of about 7.4.

Also provided herein is a needleless injector or a prefilled syringe comprising an aqueous solution formulated for intramuscular injection, the aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); and between about 0.5 to about 1.5 mg zinc. In another embodiment, a needleless injector or a prefilled syringe comprises an aqueous solution which comprises about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4.

Also provided herein is a needleless injector or a prefilled syringe comprising an aqueous solution formulated for injection, the aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate. In another embodiment, a needleless injector or a prefilled syringe comprises an aqueous solution which comprises about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); 10 mg pantothenic acid (vitamin B5); and about 0.1 mg Zinc sulfate heptahydrate, where the pH has been adjusted to about 7.4.

Also provided herein is a container, which contains a composition prepared for direct injection of a substance into a muscle, wherein the composition is an aqueous solution consisting of water-soluble components. Also provided herein is a container, which contains a composition prepared for direct injection, wherein the composition is an aqueous solution consisting of water-soluble components. Volumes to be considered for packaging in the containers include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, and about 5.0 ml.

In one aspect, the container comprises a composition comprising an aqueous solution formulated for intramuscular injection, the aqueous solution formulated for intramuscular injection comprising cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); and zinc. In one aspect, the container is an ampoule, vial, a needleless injection device or pre-filled syringe. Containers described herein may, in some instances, contain a UV-blocking agent which helps prevent degradation of components of the compositions. In one embodiment, a container comprises an aqueous solution which comprises between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); and between about 0.5 to about 1.5 mg zinc. In another embodiment, a container comprises an aqueous solution which comprises about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4.

In one aspect, the container comprises a composition comprising an aqueous solution formulated for injection, the aqueous solution formulated for injection comprising cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); pantothenic acid (vitamin B5); and Zinc sulfate heptahydrate. In one aspect, the container is an ampoule, vial, a needleless injection device or pre-filled syringe. Containers described herein may, in some instances, contain a UV-blocking agent which helps prevent degradation of components of the compositions. In one embodiment, a container comprises an aqueous solution which comprises between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate. In another embodiment, a container comprises an aqueous solution which comprises about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); 10 mg pantothenic acid (vitamin B5); and about 0.1 mg Zinc sulfate heptahydrate, where the pH has been adjusted to about 7.4.

Provided herein is a method of promoting vitality and well-being in a human patient, the method comprising administering a vitamin B supplement composition formulated for intramuscular injection, wherein the vitamin B supplement composition is administered intramuscularly to the human patient.

Provided herein is a method of promoting vitality and well-being in a human patient, the method comprising administering a vitamin B supplement composition formulated for injection, wherein the vitamin B supplement composition is intravenously, intradermally, or subcutaneously, to the human patient.

Also provided herein is a method of treating or ameliorating disease or symptoms associated with a vitamin B deficiency in a human patient in need thereof, comprising administering to the patient an aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; wherein the composition is administered to the patient through subcutaneous/intradermal or intramuscular administration. In one embodiment, the patient is administered a composition comprising about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4.

Also provided herein is a method of treating or ameliorating disease or symptoms associated with a vitamin B deficiency in a human patient in need thereof, comprising administering to the patient an aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; wherein the composition is administered to the patient through intravenous, subcutaneous, intradermal, or intramuscular administration. In one embodiment, the patient is administered a composition comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); 10 mg pantothenic acid (vitamin B5); and about 0.1 mg Zinc sulfate heptahydrate, where the pH has been adjusted to about 7.4.

In one aspect, the disease or symptom to be treated includes those associated with a vitamin B deficiency, such as, for example, depression, dementia, fibromyalgia, gastrointestinal disorder, headaches, chronic fatigue syndrome, high stress levels, hyperthyroidism, low energy, impaired memory, beriberi, Wernicke's encephalophay, ariboflavinosis, pellagra, acne, paresthesia, microcyrtic anemia, macrocytic anemia, or a combination thereof.

Also provided herein is a method of improving wound healing in a human patient in need thereof, comprising administering to the patient an aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; wherein the composition is administered to the patient through intramuscular administration. In one embodiment, a composition may be administered prior to surgery, after surgery, or both. Surgery may be, for example, plastic surgery or reconstructive surgery. In one embodiment, the patient is administered a composition comprising about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4.

Also provided herein is a method of improving wound healing in a human patient in need thereof, comprising administering to the patient an aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; wherein the composition is administered to the patient through injection. In one embodiment, a composition may be administered prior to surgery, after surgery, or both. Surgery may be, for example, plastic surgery or reconstructive surgery. In one embodiment, the patient is administered a composition comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); 10 mg pantothenic acid (vitamin B5); and about 0.1 mg Zinc sulfate heptahydrate, where the pH has been adjusted to about 7.4.

Also provided herein is a method of improving skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent in human patient in need thereof, comprising administering to the patient an aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; wherein the composition is administered to the patient through intramuscular administration. In one embodiment, the patient is administered a composition comprising about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4.

Also provided herein is a method of improving skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent in human patient in need thereof, comprising administering to the patient an aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; wherein the composition is administered to the patient through injection. In one embodiment, the patient is administered a composition comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); about 10 mg pantothenic acid (vitamin B5); and about 0.1 mg Zinc sulfate heptahydrate, where the pH has been adjusted to about 7.4.

Embodiments described herein relate to vitamin supplement compositions and injectable hyaluronic acid (HA) formulated for intradermal injection and tropical use.

There exists a need for vitamin combined with injectable HA formulations. The present inventors have developed new vitamin and injectable HA compositions formulated for intradermal injection and also topical use that serve for aesthetic enhancement purpose. Included in the formulations described herein are new formulations that are designed to improve skin condition, enhance skin texture, and appearance. For example, administration of a composition provided herein may improve skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

In one aspect, provided herein is an aqueous solution adapted for human administration, the aqueous solution comprising between about 1500 to about 5000 mcg cobalamin (vitamin B12); between about 100 to about 200 mg ascorbic acid (vitamin C); between about 10 to about 60 mg nicotinamide (vitamin B3); between about 2 to about 10 mg thiamine hydrochloride (vitamin B1); between about 0.1 to about 0.25 mg pyridoxine HCl (vitamin B6); between about 2 to about 10 mg riboflavin 5-phosphate sodium (vitamin B2); between about 0.1 to about 0.5 mg zinc sulfate heptahydrate; 2.4-12 mg/ml HA; optionally lidocaine with epinephrine; a chemical stabilizer; and optionally a preservative. Preservatives and chemical stabilizers may be added to the compositions in an amount of between about 0.01% and about 2% of the total volume.

In one embodiment, the product comprises an aqueous solution comprising about 5000 mcg cobalamin (vitamin B12); about 200 mg ascorbic acid (vitamin C); about 40 mg nicotinamide (vitamin B3); about 6 mg thiamine (vitamin B1); about 0.1 mg pyridoxine HCl (vitamin B6); about 3.6 mg riboflavin 5-phosphate sodium (vitamin B2); about 0.1 mg zinc sulfate heptahydrate; and about 12 mg/ml HA. A product provided herein may, in some instances, contain three, four, five, six, or all 8 of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); zinc sulfate heptahydrate; and diluted HA.

There exists a need for vitamins combined with hyaluronic acid, collagen, botulinum toxin, platelet-rich plasma and/or poly-L-lactic acid. The present inventors have developed formulations for intradermal injection and also topical use that serve aesthetic enhancement purposes. Included in the formulations described herein are new formulations that are designed to improve skin condition, enhance skin texture, and appearance. For example, administration of a composition provided herein may improve skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

In one aspect, provided herein is an aqueous solution adapted for human administration, the aqueous solution comprising between about 1500 to about 5000 mcg cobalamin (vitamin B12); between about 100 to about 200 mg ascorbic acid (vitamin C); between about 10 to about 60 mg nicotinamide (vitamin B3); between about 2 to about 10 mg thiamine hydrochloride (vitamin B1); between about 0.1 to about 0.25 mg pyridoxine HCl (vitamin B6); between about 2 to about 10 mg riboflavin 5-phosphate sodium (vitamin B2); between about 0.1 to about 0.5 mg zinc sulfate heptahydrate; 2.4-12 mg/ml HA; optionally lidocaine with epinephrine; a chemical stabilizer; and optionally a preservative. Preservatives and chemical stabilizers may be added to the compositions in an amount of between about 0.01% and about 2% of the total volume.

In one embodiment, the product comprises an aqueous solution comprising about 5000 mcg cobalamin (vitamin B12); about 200 mg ascorbic acid (vitamin C); about 40 mg nicotinamide (vitamin B3); about 6 mg thiamine (vitamin B1); about 0.1 mg pyridoxine HCl (vitamin B6); about 3.6 mg riboflavin 5-phosphate sodium (vitamin B2); about 0.1 mg zinc sulfate heptahydrate; about 12 mg/ml HA, and any concentration of, collagen, botulinum toxin, platelet-rich plasma (PRP), and/or poly-L-lactic acid (PLLA) as determined necessary to achieve aesthetic goals set by the doctor and patient. A product provided herein may, in some instances, contain three, four, five, six, or all of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); zinc sulfate heptahydrate; and hyaluronic acid (HA), collagen, botulinum toxin, platelet-rich plasma (PRP), and/or poly-L-lactic acid (PLLA).

Presented herein are microneedle devices for transdermal drug delivery of drug compositions. A microneedle array may be used to deliver a drug directly to the dermis, the second layer of skin. The microneedles in the array puncture the epidermal barrier and deliver the drug directly to the dermis to maximize diffusion to the bloodstream and absorption by the body's active tissues. This delivery method has an advantage over oral delivery because it allows the drug to be absorbed into the body without coming into contact with powerful digestive enzymes of the stomach, over injectable delivery because it is comparatively painless, and over topical delivery because it allows for much greater absorption of the delivered drug (Sullivan S P, Murthy N, Prausnitz M R: Minimally invasive protein delivery with rapidly dissolving polymer microneedles. Adv Mat. 2008 March; 20(5):933-938. PubMed PMCID: PMC3519393). The microneedle array will be attached a reservoir that will contain the drugs to be delivered, and this reservoir will itself be attached to contain an apparatus to encourage flow of the drug solution contained in the reservoir through the microneedles and into the skin.

Microneedle injections are used today for percutaneous delivery of bioactive agents, such as medicines or cosmetics, to the body. The advantages of these methods of delivery over others are as follows: it allows the delivered substances to be absorbed by the body without being altered by digestive enzymes, as would occur if an oral delivery method were used; it is relatively painless, as opposed to intramuscular or subcutaneous injections; and it facilitates rapid diffusion of the delivered substance through the dermis, as the microneedles physically penetrate the barrier of the epidermis, which traditional topical delivery methods do not (US Publication Number: US 2012-0296280 A1, entitled "Microneedle and Microneedle Device"). Presented herein is a method of improving skin health using microneedle delivery of certain bioactive formulations composed of hyaluronic acid, botulinum toxin, collagen, vitamins, minerals, minoxidil, platelet-rich plasma (PRP), and/or poly-L-lactic acid (PLLA).

A microneedle array may be used to deliver hyaluronic acid, botulinum toxin, collagen, vitamins, minerals, minoxidil, platelet-rich plasma (PRP), and/or poly-L-lactic acid (PLLA) or any combination thereof, directly to the dermis, the second layer of skin. The microneedles puncture the epidermal barrier and deliver the desired substances directly to the dermis for faster, more efficient and more effective absorption by the skin. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis. The formulations composed of hyaluronic acid, botulinum toxin, collagen, vitamins, minerals, minoxidil, platelet-rich plasma (PRP), and/or poly-L-lactic acid (PLLA) act on the skin and/or subcutaneous muscles in order to boost cell rejuvenation and creation, alleviate fine lines and wrinkles, reduce the appearance of scars and blemishes, and improve skin clarity, elasticity, firmness, tone, vitality, and overall health.

Provided herein is a method of aesthetically enhancing a subject in need thereof, comprising administering to the subject an aqueous solution described herein. In one aspect, the solutions for aesthetically enhancing a subject improve skin condition, enhance skin texture, appearance, or a combination thereof. The solutions may improves skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

This application incorporates the specification of U.S. application Ser. No. 13/575,525, entitled "MICRO NEEDLE AND MICRO NEEDLE DEVICE", filed on Jul. 26, 2012, and which published as US 2012-0296280 A1 on Nov. 22, 2012, by reference in its entirety.

DETAILED DESCRIPTION OF THE INVENTION

Unless otherwise defined, all technical and scientific terms used herein have the same meaning as commonly understood by one of ordinary skill in the art. Methods and materials are described herein for use in the present embodiments; other, suitable methods and materials known in the art can also be used. The materials, methods, and examples are illustrative only and not intended to be limiting. In case of conflict, the present specification, including definitions, will control.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 2%, 3%, 4%, or 5% of a particular term.

The term "aging-related skin condition" relates to any skin condition or disorder associated with, caused by, or affected by, intrinsic aging and/or extrinsic aging. Aging-related skin conditions that may be treated using the present methods and formulations include, but are not limited to, wrinkles, age spots, sun damage (particularly UV radiation-induced oxidative stress), blemishes, hyperpigmented skin, age spots, increased skin thickness, loss of skin elasticity and collagen content, dry skin, lentigines, melasmas, as well as scars.

Vitamin B12, also called cobalamin, is a water-soluble vitamin with a key role in the normal functioning of the brain and nervous system, and for the formation of blood. It is one of the eight B vitamins. It may be involved in the metabolism of every cell of the human body, especially affecting DNA synthesis and regulation, but also fatty acid synthesis and energy production. Vitamin B12 may also be involved in maintenance of the central nervous system and has been used to affect memory loss, Alzheimer's disease, boosting mood, energy and concentration, boost the immune system, and slow aging. Vitamin B12 may also play a role in heart disease, lowering high homocysteine levels (which may contribute to heart disease), male infertility, diabetes, sleep disorders, depression, mental disorders, weak bones (osteoporosis), swollen tendons, AIDS, inflammatory bowel disease, asthma, allergies, a skin disease called vitiligo, preventing cervical and other cancers, and skin infections. Two common forms of Vitamin B12 are cyanocobalamin and methylcobalamin.

Vitamin B12 deficiency may cause macrocytic anemia, fatigue, loss of appetite, loss of balance, weakness, and mood disturbances. It also may cause serious neurologic and neuropsychiatric illness such as paresthesias, ataxia, and memory loss. Vitamin B12 absorption may be impaired at the level of the stomach, where intrinsic factor is produced, or at the level of the terminal ileum, where intrinsic factor bound to vitamin B12 is absorbed.

Niacin and nicotinamide, also known as niacinamide, are forms of vitamin B3. Nicotinamide is the amide of nicotinic acid (vitamin B3/niacin). Nicotinamide is a water-soluble vitamin and is part of the vitamin B group. Nicotinamide may be used for preventing vitamin B3 deficiency and related conditions such as pellagra. Each of these forms of vitamin B3 may be used for schizophrenia, hallucinations due to drugs, Alzheimer's disease and age-related loss of thinking skills, chronic brain syndrome, depression, motion sickness, alcohol dependence, and fluid collection (edema).

Vitamin B1, also known as thiamine, is a water-soluble vitamin and may be utilized for metabolizing carbohydrates and production of energy. Vitamin B1 also may aids in the function of the heart and cardiovascular system and the nervous system.

Vitamin B6, also known as pyridoxine, may be involved in many aspects of macronutrient metabolism, neurotransmitter synthesis, histamine synthesis, hemoglobin synthesis and function and gene expression. Vitamin B6 may assist with cellular metabolism, supports the immune system, with formation of red blood cells and maintenance of healthy brain function. Vitamin B6 may be used for Alzheimer's disease, attention deficit-hyperactivity disorder (ADHD), Down syndrome, autism, diabetes and related nerve pain, sickle cell anemia, migraine headaches, asthma, carpal tunnel syndrome, night leg cramps, muscle cramps, arthritis, allergies, acne and various other skin conditions, and infertility. It is also may be used to treat dizziness, motion sickness, preventing the eye disease age-related macular degeneration (AMD), seizures, convulsions due to fever, and movement disorders (tardive dyskinesia, hyperkinesis, chorea), as well as for increasing appetite and helping people remember dreams. Vitamin B6 may be used for acne, leprosy, attention deficit-hyperactivity disorder (ADHD), memory loss, arthritis, preventing premenstrual headache, improving digestion, protecting against toxins and pollutants, reducing the effects of aging, lowering blood pressure, improving circulation, promoting relaxation, improving orgasm, and preventing cataracts. Vitamin B6 deficiency may cause anemia due to insufficient production of hemoglobin.

Vitamin B2, also known as riboflavin, releases energy from carbohydrates and may be used for preventing low levels of riboflavin (riboflavin deficiency), cervical cancer, and migraine headaches. It also may be used for treating riboflavin deficiency, acne, muscle cramps, burning feet syndrome, carpal tunnel syndrome, and blood disorders such as congenital methemoglobinemia and red blood cell aplasia. It also may be used for increasing energy levels; boosting immune system function; maintaining healthy hair, skin, mucous membranes, and nails; slowing aging; boosting athletic performance; promoting healthy reproductive function; canker sores; memory loss, including Alzheimer's disease; ulcers; burns; alcoholism; liver disease; sickle cell anemia; and treating lactic acidosis brought on by treatment with a class of AIDS medications called NRTI drugs.

The term "vitamin B6" encompasses multiple forms of vitamin B6 suitable for human administration. Several forms of the vitamin are known, but pyridoxal phosphate (PLP; "pyridoxine") is the active form and may be used as a cofactor in many reactions of amino acid metabolism, including transamination, deamination, and decarboxylation. Pyridoxine may be used in enzymatic reactions affecting the release of glucose from glycogen.

Vitamin C, also known as ascorbic acid, is an antioxidant. Vitamin C may be used to protect against free radicals and promote a healthy immune system, wound healing, and forming healthy skin. More specifically, ascorbic acid may be used to prevent and treat scurvy, a disease caused by a lack of vitamin C in the body. People with high intakes of vitamin C from fruits and vegetables may have a lower risk of getting many types of cancer, such as lung, breast, and colon cancer.

Vitamin B5, also known as pantothenic acid, has skincare benefits. For example, it increases the degree of hydration of the skin, reduce the trans-epidermal water loss and keep the elasticity and smoothness of the skin. Vitamin B5 may be used in acne treatments and may be used to reduce itchiness of the skin.

Zinc is an essential mineral found in cells throughout the body. Zinc is required for protein synthesis and collagen formation, and may be used to promote a healthy immune system and assist in wound healing. It may also be used for muscular growth and contraction and to protect the liver from chemical damage such as which can occur with anesthetics or other drugs or toxins. Zinc may also be utilized in bone formation. Zinc deficiency may contribute to fatigue, susceptibility to infection, and slow wound healing.

Hyaluronic acid is involved in cartilage resilience and skin repair, has been applied medically for decades for a number of different uses. Among the most common of these medical applications employ injectable delivery, for example to treat joint pain, or topical delivery, for example to treat dermatitis. Cosmetically, it is often used as an active agent in facial filler injections to smooth wrinkles and in topical creams and gels to rejuvenate the skin and combat the aging process.

Vitamins and minerals, or vital nutrients, are not synthesized in the human body and must be obtained from the diet for normal metabolic functioning. While they occur naturally in food, vitamins and minerals are often also taken as oral, injectable, or topical supplements to make up for dietary imbalance or to achieve specific physical effects. The most common vitamins used today to promote skin health are A, B, C, D, and E, while the most common minerals used include zinc and calcium.

Collagen is a type of fibrous protein found most often in the skin, flesh, and connective tissue of vertebrates. In mammals, it is the most abundant protein in the body, and provides structural support for major tissues and organs. In the skin, it is responsible for providing structure, firmness, and smoothness, and it is often a decrease in collagen production that leads to chronic aging. For this reason, collagen is often injected or topically introduced to the skin in attempts to slow or reverse the effects of aging (Varani J, Dame M K, Rittie L, Fligiel S E G, Kang S, Fisher G J, Voorhees J J: Decreased Collagen Production in Chronically Aged Skin. Am J Pathol. 2006 June; 168(6):1861-1868. PubMed PMCID: PMC1606623).

Botulinum toxinum, a neurotoxic protein, is used cosmetically and therapeutically for treatment of facial lines and wrinkles, upper motor neuron syndrome, excessive sweating, cervical dystonia, chronic migraine, and overactive bladder. The toxin is generally injected into the subcutaneous muscles at the target areas, and works by temporarily (for a period of six weeks to eight months, depending on the location and the dose) inhibiting the release of acetylcholine at the neuromuscular junction and thus paralyzing the muscles achieve the desired affects (BOTOX (onabotulinumtoxinA) [prescribing information]. Irvine, Calif. Allergan, Inc. January 2013).

Minoxidil is a vasodilator that was originally administered orally as a treatment for hypertension, but was found to have the additional effect of slowing hair loss and promoting hair growth. It is now a common topical treatment for androgenic hair loss, and is thought to achieve hair regrowth by increasing the blood flow (and thus the availability of oxygen and vital nutrients) to the hair follicles, stimulating them to resume normal functioning (Olsen E A, Whiting D, Bergfeld W, Miller J, Hordinsky M, Wanser R, Zhang P, Kohut B: A multicenter, randomized, placebo-controlled, double-blind clinical trial of a novel formulation of 5% minoxidil topical foam versus placebo in the treatment of androgenetic alopecia in men. J Am Acad Dermatol. 2007 Aug. 29. PubMed PMID: 17761356).

Platelet-rich plasma (PRP) is blood plasma that has been enriched by platelets, and is prepared by separating whole blood via centrifugation and then collecting the plasma-rich layers that emerge. Because it has five times the baseline platelet concentration of plasma (~100,000 platelets per microliter as opposed to the baseline of ~20,000 platelets per microliter), it contains a number of different growth factors (proteins that stimulate tissue growth, the release of which can be induced by the addition of thrombin and calcium chloride. PRP injections have been used clinically for several years as a treatment for nerve, bone, and muscle injuries, and have been used cosmetically to reverse damage to the skin and to promote dermal strength and rejuvenation (Borrione P, Gianfrancesco A D, Pereira M T, Pigozzi F: Platelet-rich plasma in muscle healing. Am J Phys Med Rehabil. 2010 October; 89(10):854-61. PubMed PMID: 20855985).

Poly-L-lactic Acid (PLLA) is a type of dermal filler used in the treatment of facial lipoatrophy (the gradual loss of facial fat, generally due to aging). PLLA, upon entering the skin, provides immediate structural support to the skin and also promotes the neo-synthesis of collagen, hiding sunken areas. Over time, it converted by the body into harmless lactic acid, gradually transferring the load to the recently synthesized collagen (SCULPTRA Aesthetic (injectable poly-L-lactic acid) [prescribing information]. Bridgewater, N.J. Sanofi-Aventis U.S. LLC. May 2012).

Microneedle injections are used today for the delivery of substances, such as medicines or cosmetics, through the skin to the body. There are certain advantages of this delivery method over others: it increases absorption of the substance as compared to an oral delivery method by allowing the substance to be introduced to the body without first exposing it to a hostile digestive environment; it decreases the pain associated with delivery of the substance as compared to intramuscular or subcutaneous injections by minimizing trauma to the skin and underlying tissues; and it allows for more rapid diffusion of the delivered substance through the dermis as compared to traditional topical delivery methods, as the microneedles physically penetrate the epidermis.

Compositions

Compositions described herein may be used to treat one or more clinical manifestations and/or symptoms of a disease or skin condition, hair loss, wound healing and/or prevention of scarring, or for anti-aging, longevity and wellness purpose described herein. The present inventors have identified new compositions that may be injected into a patient to improve skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent, etc. The compositions and methods provided herein provide vitamin compositions formulated for intramuscular injection, subcutaneous injection, or intradermal injection. The compositions and methods provided herein provide vitamin compositions formulated for injection, such as subcutaneous injection, intravenous injection, intramuscular injection or intradermal injection. For vitamin supplementation to be effective, the supplements provided to a patient should contain suitable amounts of the various micronutrients required by the patient. Suitable amounts can be determined by the skilled physician and depend on the age, gender and general health of the patient, as well as a surgical, or other procedure planned for the patient. In some cases, it may also be determined based upon the degree and type of trauma a patient has suffered. Previous nutritional status may also be considered when determining a suitable amount of nutritional supplementation. In addition, patient compliance is a very important factor, since nutritional supplementation is not effective if the patient does not receive the supplements and is much less effective if the patient does not receive the proper dose on a consistent basis.

Vitamin supplementation may be provided in easy-to-use and clearly labeled packs to increase patient compliance. The supplements may be administered to any patient needing, e.g., improvement of a skin condition such as, for example, skin elasticity, skin regeneration, metabolism, etc. For example, patient populations include, but are not limited to: men over age fifty, and women over age fifty. That is, patients whose skin may not be as elastic or firm as a younger patient. However, it would be understood that humans under the age of fifty may also experience changes in their skin which would benefit from administration of a composition described herein. For example, a patient who may also be administered a composition described herein may be one who had plastic or reconstructive surgery, which population includes any human of any age. In addition to these compositions, a treating physician may add other disease-specific supplements as the patient's condition warrants. In addition to the pre-packaged nutritional supplements, the dispensing physician may add one or more other specific supplements, if needed.

Vitamins which may be used in a composition (formulation) described herein include, but are not limited to, B1 (thiamine), B2 (riboflavin), B3 (niacin), B5 (pantothenic acid), B6 (pyridoxine), B7 (biotin), B12 (cobalamin) and folic acid.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc, and optionally a chemical stabilizer and optionally a preservative, wherein the aqueous solution is formulated for intramuscular injection. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), and zinc. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), and zinc. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), and zinc. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), and zinc. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), and zinc.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5); Zinc sulfate heptahydrate, and optionally a chemical stabilizer and optionally a preservative, wherein the aqueous solution is formulated for intramuscular injection. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc sulfate heptahydrate. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc sulfate heptahydrate. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc sulfate heptahydrate. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc sulfate heptahydrate. In another embodiment, a composition contains only seven of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc Sulfate Heptahydrate. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc sulfate heptahydrate.

Vitamin B12 may be included in a composition in amount to increase metabolism, or improve mental health. In one embodiment, the aqueous solution comprises from about 500 to about 1500 mcg cobalamin, from about 750 to about 1250 mcg cobalamin, or from about 900 to about 1000 mcg cobalamin. In one embodiment, vitamin B12 is present in a composition in an amount of about 1000 mg. One would appreciate that vitamin B12 exists in multiple forms suitable for therapeutic use, including cyanocobalamin and methylcobalamin, which forms are contemplated for use herein.

Vitamin B12 may be included in a composition in amount to increase metabolism, or improve mental health. In one embodiment, the aqueous solution comprises from about 1500 to about 6250 mcg cobalamin, from about 4000 to about 5000 mcg cobalamin, or from about 3000 to about 4500 mcg cobalamin. In one embodiment, vitamin B12 is present in a composition in an amount of about 5000 mg. One would appreciate that vitamin B12 exists in multiple forms suitable for therapeutic use, including cyanocobalamin and methylcobalamin, which forms are contemplated for use herein.

Vitamin B3 (nicotinamide) may be included in a composition in amount of from about 10 to about 60 mg, from about 20 to about 50 mg, from or about 30 to about 40 mg. In one embodiment, thiamine is present in a composition in an amount of about 40 mg.

Vitamin B3 (nicotinamide) may be included in a composition in amount of from about 30 to about 50 mg, from about 20 to about 40 mg, from or about 35 to about 45 mg. In one embodiment, thiamine is present in a composition in an amount of about 40 mg.

Vitamin B1 may be included in a composition in an amount of from about 2 to about 10 mg, from about 4 to 8 mg, or from about 4 to about 6 mg. In one embodiment, thiamine is present in a composition in an amount of about 6 mg.

Vitamin B1 may be included in a composition in an amount of from about 4.5 to about 7.5 mg, from about 5 to 7 mg, or from about 5.5 to about 6.5 mg. In one embodiment, thiamine is present in a composition in an amount of about 6 mg.

Vitamin B6 (pyridoxine) may be included in a composition in an amount of from about 2 to about 10 mg, about 4 to 8 mg, or about 4 to about 6 mg. Pyridoxine may be administered as pyridoxine HCl. In one embodiment, pyridoxine HCl is present in a composition in an amount of about 6 mg.

Vitamin B6 (pyridoxine) may be included in a composition in an amount of from about 0.1 to about 0.3 mg, about 0.15 to 0.2 mg, or about 0.2 to about 0.25 mg. Pyridoxine may be administered as pyridoxine HCl. In one embodiment, pyridoxine HCl is present in a composition in an amount of about 0.1 mg.

Vitamin B2 (Riboflavin 5-phosphate sodium) may be included in a composition in an amount of from about 2 to about 10 mg, from about 4 to about 8 mg or from about 4 to about 6 mg. In one embodiment, riboflavin 5-phosphate sodium is present in a composition in an amount of about 3.6 mg.

Vitamin B2 (Riboflavin 5-phosphate sodium) may be included in a composition in an amount of from about 2.7 to about 4.5 mg, from about 3 to about 4 mg or from about 3.5 to about 4.5 mg. In one embodiment, riboflavin 5-phosphate sodium is present in a composition in an amount of about 3.6 mg.

Vitamin C (ascorbic acid) may be included in a composition in an amount of from about 50 to about 300 mg, from about 100 to about 250 mg, or from about 150 to about 200 mg. In one embodiment, ascorbic acid is present in a composition in an amount of about 200 mg.

Vitamin C (ascorbic acid) may be included in a composition in an amount of from about 150 to about 250 mg, from about 170 to about 230 mg, or from about 180 to about 200 mg. In one embodiment, ascorbic acid is present in a composition in an amount of about 200 mg.

Vitamin B5 (pantothenic acid) maybe included in a composition in an amount of from about 7.5 to 15 mg, from about 8 to 12 mg, or from about 10 to 15 mg. in one embodiment, pantothenic acid is present in a composition in an amount of about 10 mg.

Zinc may be included in a composition in an amount of from about 0.25 to about 2.0 mg, or from about 1.0 to about 1.5 mg. In one embodiment, zinc is present in a composition in an amount of about 1 mg.

Zinc sulfate heptahydrate may be included in a composition in an amount of from about 0.08 to about 0.125 mg, or from about 0.1 to about 0.125 mg. In one embodiment, zinc is present in a composition in an amount of about 0.1 mg.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

The aqueous solution may optionally include a preservative. Any number of preservatives may be used to increase shelf-life of injectable formulations. Non-limiting examples of preservatives are, for example, benzyl alcohol, methylparaben, propylparben, Benzyl alcohol, thimerosal, m-Cresol and methyl p-hydroxybenzoate. In one embodiment, benzyl alcohol also acts as a mild anesthetic potential that may mitigate the pain of injection.

An aqueous solution may include a bioactive agent in order to increase the ability of a formulation to achieve patient-specified intended results. Non-limiting examples of additional bioactive agents are hyaluronic acid, botulinum toxin, platelet-rich plasma (PRP), and polylactic acid. It would be understood that these bioactive agents may be combined with any of the other solution components described herein.

Solution formulations can be prepared by dissolving these components in an aqueous buffer known in the art of solution formulations such as phosphate buffers and/or citrate buffers.

In one aspect, provided herein is an aqueous vitamin composition which is specifically tailored for intramuscular injection. A vitamin composition which is specifically tailored for intramuscular injection generally refers to a composition prepared for direct injection of a substance into a muscle in an amount appropriate for intramuscular injection.

In one aspect, provided herein is an aqueous vitamin composition which is specifically tailored for injection. A vitamin composition which is specifically tailored for injection generally refers to a composition prepared for direct injection of a substance into a muscle in an amount appropriate for injection.

Supplement compositions suitable for intramuscular injection can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Supplement compositions suitable for injection can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Sterile injectable solutions can be prepared by incorporating the vitamin component in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Provided herein a composition described herein for patients undergoing or who have undergone a surgical procedure, or who have suffered an injury. The composition is designed to prevent deficiencies in vitamin B needed for optimal health and healing during the period pre- and post-surgery or for general application and to enable the patient receiving the composition to achieve maximum healing and rapid recovery from a procedure or injury. In one embodiment, surgery is plastic surgery or reconstructive surgery.

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means an acceptable material, composition or vehicle, such as a liquid or solid filler, diluent, excipient, and/or solvent involved in carrying or transporting the subject compounds from the administration site of one organ, or portion of the body, to another organ, or portion of the body. Each carrier is acceptable in the sense of being compatible with the other ingredients of the formulation and not injurious to a subject to whom it is administered. Nor should an acceptable carrier alter the specific activity of the subject compounds.

Provided herein is an aqueous solution containing the following ingredients: from about 500 to about 1500 mcg cobalamin (vitamin B12); from about 100 to about 200 mg ascorbic acid (vitamin C); from about 10 to about 60 mg nicotinamide (vitamin B3); from about 2 to about 10 mg thiamine (vitamin B1); from about 2 to about 10 mg pyridoxine HCl (vitamin B6); from about 2 to about 10 mg riboflavin 5-phosphate sodium (vitamin B2); from about 0.5 to about 1.5 mg zinc; and about 1 ml q.s., sterile water for injection. The aqueous solution is formulated in physiological saline and adjusted to an acceptable pH, thereby minimizing any injecting pain beyond the needle prick. The aqueous solution may be optionally supplemented with a preservative (e.g., benzyl alcohol) and/or a chemical stabilizer (e.g., gentisic acid), depending on anticipated shelf-life. In one embodiment, the volume that is injected intramuscularly is about 1 ml.

Provided herein is an aqueous solution containing the following ingredients: from about 1500 to about 6250 mcg cobalamin (vitamin B12); from about 150 to about 250 mg ascorbic acid (vitamin C); from about 30 to about 50 mg nicotinamide (vitamin B3); from about 4.5 to about 7.5 mg thiamine (vitamin B1); from about 0.1 to about 0.3 mg pyridoxine HCl (vitamin B6); from about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; and about 1 ml q.s., sterile water for injection. The aqueous solution is formulated in physiological saline and adjusted to an acceptable pH, thereby minimizing any injecting pain beyond the needle prick. The aqueous solution may be optionally supplemented with a preservative (e.g., benzyl alcohol) and/or a chemical stabilizer (e.g., gentisic acid), depending on anticipated shelf-life. In one embodiment, the volume that is injected is about 1 ml.

Provided herein is an aqueous solution comprising the following ingredients: about 1000 mcg cobalamin (vitamin B12); about 200 mg ascorbic acid (vitamin C); about 40 mg nicotinamide (vitamin B3); about 6 mg thiamine (vitamin B1); about 6 mg pyridoxine HCl (vitamin B6); about 3.6 mg riboflavin 5-phosphate sodium (vitamin B2); about 1 mg zinc; and about 1 ml q.s., sterile water for injection. The aqueous solution is formulated in physiological saline and adjusted to an acceptable pH, thereby minimizing any injecting pain beyond the needle prick. In addition, the aqueous solution may be optionally supplemented with a preservative (e.g., benzyl alcohol) and/or a chemical stabilizer (e.g., gentisic acid), depending on anticipated shelf-life.

Provided herein is an aqueous solution comprising the following ingredients: about 5000 mcg cobalamin (vitamin B12); about 200 mg ascorbic acid (vitamin C); about 40 mg nicotinamide (vitamin B3); about 6 mg thiamine (vitamin B1); about 0.1 mg pyridoxine HCl (vitamin B6); about 3.6 mg riboflavin 5-phosphate sodium (vitamin B2); about 10 mg pantothenic acid (vitamin B5); and about 0.1 mg Zinc sulfate heptahydrate; and about 1 ml q.s., sterile water for injection. The aqueous solution is formulated in physiological saline and adjusted to an acceptable pH, thereby minimizing any injecting pain beyond the needle prick. In addition, the aqueous solution may be optionally supplemented with a preservative (e.g., benzyl alcohol) and/or a chemical stabilizer (e.g., gentisic acid), depending on anticipated shelf-life.

Compositions described herein may be used to treat one or more clinical manifestations and/or symptoms aging related skin problems. The present inventors have identified new compositions that may be applied topically or injected into a patient to improve skin elasticity, skin luminosity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, etc. The compositions and methods provided herein provide vitamin and HA compositions formulated for topical use or intradermal injection. For vitamin and HA composition to be effective, the compositions provided to a patient should contain suitable amounts of the various micronutrients and HA required by the patient. Suitable amounts can be determined by the skilled physician and depend on the age, gender and general health of the patient, as well as a surgical, or other procedure planned for the patient. In some cases, it may also be determined based upon the degree of the aging stage. Previous skincare procedures may also be considered when determining a suitable amount of aesthetic composition. In addition, patient compliance is a very important factor, since aesthetic composition is not effective if the patient does not receive the composition and is much less effective if the patient does not receive the proper dose on a consistent basis.

Provided herein are composition of vitamins and HA for treating facial fine lines, for both intradermal and topical use. These compositions represent an advance over compositions currently on the market; the commercial products are less likely used in treating facial fine lines, but rather, are more often applied in treatment of deep facial lines.

Vitamins and HA which may be used in a composition (formulation) described herein include, but are not limited to, B1 (thiamine), B2 (riboflavin), B3 (niacin), B5 (pantothenic acid), B6 (pyridoxine), B7 (biotin), B12 (cobalamin), diluted HA, lidocaine, epinephrine and folic acid.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, diluted HA, and optionally lidocaine with epinephrine, a chemical stabilizer and optionally a preservative, wherein the aqueous solution is formulated for topical use and/or dermal injection. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, diluted HA, and lidocaine with epinephrine. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, diluted HA, and lidocaine with epinephrine. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, diluted HA, and lidocaine with epinephrine. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, diluted HA, and lidocaine with epinephrine. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, diluted HA, and lidocaine with epinephrine.

Vitamin B12 may be included in a composition in amount to improve skin appearance. In one embodiment, the aqueous solution comprises from about 2500 to about 3000 mcg cobalamin, from about 3500 to about 4500 mcg cobalamin, or from about 4000 to about 5000 mcg cobalamin. In one embodiment, vitamin B12 is present in a composition in an amount of about 5000 mg. One would appreciate that vitamin B12 exists in multiple forms suitable for therapeutic use, including cyanocobalamin and methylcobalamin, which forms are contemplated for use herein.

Vitamin B3 (nicotinamide) may be included in a composition in amount of from about 10 to about 60 mg, from about 20 to about 50 mg, from or about 30 to about 40 mg. In one embodiment, thiamine is present in a composition in an amount of about 40 mg.

Vitamin B1 may be included in a composition in an amount of from about 2 to about 10 mg, from about 4 to 8 mg, or from about 4 to about 6 mg. In one embodiment, thiamine is present in a composition in an amount of about 6 mg.

Vitamin B6 (pyridoxine) may be included in a composition in an amount of from about 0 to about 0.2 mg, about 0 to 0.1 mg, or about 0.1 to about 0.2 mg. Pyridoxine may be administered as pyridoxine HCl. In one embodiment, pyridoxine HCl is present in a composition in an amount of about 0.1 mg.

Vitamin B2 (Riboflavin 5-phosphate sodium) may be included in a composition in an amount of from about 2 to about 10 mg, from about 4 to about 8 mg or from about 4 to about 6 mg. In one embodiment, riboflavin 5-phosphate sodium is present in a composition in an amount of about 3.6 mg.

Vitamin C (ascorbic acid) may be included in a composition in an amount of from about 50 to about 300 mg, from about 100 to about 250 mg, or from about 150 to about 200 mg. In one embodiment, ascorbic acid is present in a composition in an amount of about 200 mg.

Zinc sulfate heptahydrate may be included in a composition in an amount of from about 0 to about 0.2 mg, or from about 0 to about 0.1 mg. In one embodiment, zinc is present in a composition in an amount of about 0.1 mg.

Diluted hyaluronic acid (HA) may be included in a composition in an amount of from about 2.4 mg/ml to about 12 mg/ml, or from about 4.8 mg/ml to about 7.2 mg/ml. In one embodiment, the diluted HA is present in a composition in an amount of about 4.8 mg/ml.

The aqueous solution may optionally include lidocaine with epinephrine, which are used for providing patient comfort and reduce bruising.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

Solution formulations can be prepared by dissolving these components in an aqueous buffer known in the art of solution formulations such as phosphate buffers and/or citrate buffers.

Vitamin and HA compositions suitable for intradermal injection and topical use can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Sterile injectable solutions can be prepared by incorporating the vitamin component and HA in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Compositions described herein may be used to treat one or more clinical manifestations and/or symptoms aging related skin problems. The present inventors have identified new compositions that may be applied topically or injected into a patient to improve skin elasticity, skin luminosity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, etc. The compositions and methods provided herein provide bioactive compositions formulated for topical use or intradermal injection.

For these compositions to be effective, the compositions provided to a patient should contain suitable amounts of the various active agents required by the patient. Suitable amounts can be determined by the skilled physician and depend on the age, gender and general health of the patient, as well as a surgical, or other procedure planned for the patient. In some cases, it may also be determined based upon the degree of the aging stage. Previous skincare procedures may also be considered when determining a suitable amount of aesthetic composition. In addition, patient compliance is a very important factor, since aesthetic composition is not effective if the patient does not receive the composition and is much less effective if the patient does not receive the proper dose on a consistent basis.

Active ingredients which may be used in a composition (formulation) described herein include, but are not limited to, B1 (thiamine), B2 (riboflavin), B3 (niacin), B5 (pantothenic acid), B6 (pyridoxine), B7 (biotin), B12 (cobalamin), hyaluronic acid, collagen, botulinum toxin, platelet-rich plasma, poly-L-lactic acid, lidocaine, epinephrine and folic acid.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid (HA), collagen, botulinum toxin, platelet-rich plasma (PRP), poly-L-lactic acid (PLLA), and optionally lidocaine with epinephrine, a chemical stabilizer and optionally a preservative, wherein the aqueous solution is formulated for topical use and/or dermal injection. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

Vitamin B12 may be included in a composition in amount to improve skin appearance. In one embodiment, the aqueous solution comprises from about 2500 to about 3000 mcg cobalamin, from about 3500 to about 4500 mcg cobalamin, or from about 4000 to about 5000 mcg cobalamin. In one embodiment, vitamin B12 is present in a composition in an amount of about 5000 mg. One would appreciate that vitamin B12 exists in multiple forms suitable for therapeutic use, including cyanocobalamin and methylcobalamin, which forms are contemplated for use herein.

Vitamin B3 (nicotinamide) may be included in a composition in amount of from about 10 to about 60 mg, from about 20 to about 50 mg, from or about 30 to about 40 mg. In one embodiment, thiamine is present in a composition in an amount of about 40 mg.

Vitamin B1 may be included in a composition in an amount of from about 2 to about 10 mg, from about 4 to 8 mg, or from about 4 to about 6 mg. In one embodiment, thiamine is present in a composition in an amount of about 6 mg.

Vitamin B6 (pyridoxine) may be included in a composition in an amount of from about 0 to about 0.2 mg, about 0 to 0.1 mg, or about 0.1 to about 0.2 mg. Pyridoxine may be administered as pyridoxine HCl. In one embodiment, pyridoxine HCl is present in a composition in an amount of about 0.1 mg.

Vitamin B2 (Riboflavin 5-phosphate sodium) may be included in a composition in an amount of from about 2 to about 10 mg, from about 4 to about 8 mg or from about 4 to about 6 mg. In one embodiment, riboflavin 5-phosphate sodium is present in a composition in an amount of about 3.6 mg.

Vitamin C (ascorbic acid) may be included in a composition in an amount of from about 50 to about 300 mg, from about 100 to about 250 mg, or from about 150 to about 200 mg. In one embodiment, ascorbic acid is present in a composition in an amount of about 200 mg.

Zinc sulfate heptahydrate may be included in a composition in an amount of from about 0 to about 0.2 mg, or from about 0 to about 0.1 mg. In one embodiment, zinc is present in a composition in an amount of about 0.1 mg.

Hyaluronic Acid may be included in a composition in an amount of from about 2.4 mg/ml to about 12 mg/ml, or from about 4.8 mg/ml to about 7.2 mg/ml. In one embodiment, the HA is present in a composition in an amount of about 4.8 mg/ml.

Collagen, botulinum toxin, platelet-rich plasma, and poly-L-lactic acid may be included in a composition in any amount as considered necessary to achieve the aesthetic goals set by the patient and doctor.

The aqueous solution may optionally include lidocaine with epinephrine, which are used for providing patient comfort and reduce bruising.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

Solution formulations can be prepared by dissolving these components in an aqueous buffer known in the art of solution formulations such as phosphate buffers and/or citrate buffers.

Bioactive compositions suitable for intradermal injection and topical use can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Sterile injectable solutions can be prepared by incorporating the aforementioned components in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The amount of optional preservative in any of the compositions described herein may be about 0.05%, about 0.1%, about 0.25%, about 0.5%, about 0.75%, about 1.0%, about 1.25%, about 1.5%, about 1.75%, about 2%, or any integer therein.

The amount of optional chemical stabilizer in any of the compositions described herein may be about 0.05%, about 0.1%, about 0.25%, about 0.5%, about 0.75%, about 1.0%, about 1.25%, about 1.5%, about 1.75%, about 2%, or any integer therein. In one embodiment, the volume that is injected (e.g., intramuscularly) is about 1 ml.

An acceptable pH range for the formulations described herein are those which are acceptable for administration to human patients and include, but are not limited to, from about pH 6.0 to about pH 8.0, from about pH 6.5 to about pH 7.5, and from about pH 7.0 to about pH 7.5. In one embodiment, the pH is adjusted to about 7.4.

Containers

Compositions described herein may be packed into a container such as, for example, an ampoule, vial a needleless injection device or pre-filled syringe.

Provided herein is a container comprising a composition described herein prepared for direct injection of a substance into a muscle, wherein the composition is an aqueous solution consisting of water-soluble components. The vitamin compositions described herein are typically packed in a sealed and sterilized plastic or glass container. The container can be supplied in a unit dosage form such as an ampoule, vial, a needleless injection device or disposable pre-filled syringe. Containers described herein may, in some instances, contain a UV-blocking agent which help prevent degradation of components of the compositions.

Provided herein is a vial or ampoule comprising a pre-formulated vitamin solution formulated for intramuscular injection. Provided herein is a vial or ampoule comprising a pre-formulated vitamin solution formulated for injection. Also provided herein is a vial containing sterile powders for the preparation of sterile injectable solutions; methods of preparation are vacuum drying and freeze-drying, which yield a powder of the active ingredient plus any additional desired ingredient from a previously sterile-filtered solution thereof. The vial can contain a composition in sterile powders in unit dosage form which after the addition of sterile water is than stable for at least three months, at least six months or at least one year when stored at room temperature and is suitable for intramuscular injection. The vial can contain a composition in sterile powders in unit dosage form which after the addition of sterile water is than stable for at least three months, at least six months or at least one year when stored at room temperature and is suitable for injection.

Volumes to be considered for packaging in vials and ampoules include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, and about 5.0 ml.

Provided herein is a pre-filled syringe, comprising a composition described herein. Pre-filled syringes may contain 1 cc (1 ml), or up to 1.2 cc. In some embodiments, the syringe is a 1 cc or a 2 cc syringe.

Provided herein is a needleless injection device comprising a composition described herein. Needleless injection devices may contain 1 cc (1 ml), or up to 1.2 cc. In some embodiments, the syringe is a 1 cc or a 2 cc syringe.

The dosage amounts in these formulas can be modified depending on the judgment of the treating physician and the requirements of the individual patient. More specifically, the daily dosage amounts of one, some, or all of the nutritional compounds can be decreased by 5%, 10%, 20%, 30%, 40%, 50% or up to about 75% or increased by 20%, 40%, 50%, 75%, 100%, 200%, 300%, 400% or up to about 500% of the stated preferred amounts. In another embodiment, the daily dosage amounts of one, some, or all of the nutritional compounds can be decreased by 5%, 10%, 15%, 20%, 25% or up to about 30%; or increased by 10%, 15%, 20%, 25%, 30%, 40%, 50%, 75%, or up to about 100% of the stated preferred amounts.

Methods of Use

Generally, the methods include administering a therapeutically effective amount of a composition as described herein, to a subject who is in need of, or who has been determined to be in need of, such treatment.

A "subject" or "patient" (e.g., a mammal such as a human or a non-human animal) can be a mammal who exhibits one or more clinical manifestations and/or symptoms of a disease or skin condition, hair loss, wound healing and/or prevention of scarring, or for anti-aging, longevity and wellness purpose described herein. In certain situations, a subject may be asymptomatic and yet still have clinical manifestations of the disease or condition.

A physician or veterinarian can readily determine and prescribe the effective amount of the formulation required. For example, the physician or veterinarian could start doses of the compounds employed in the formulation at levels lower than that required in order to achieve the desired therapeutic effect and gradually increase the dosage until the desired effect is achieved. Alternatively, a dose can remain constant.

Provided herein is a method of promoting vitality and well-being in a human patient, the method comprising administering a vitamin B supplement composition formulated for intramuscular injection, wherein the vitamin B supplement composition is administered intramuscularly to the human patient. Compositions to be administered are described in more detail below.

Provided herein is a method of treating or ameliorating a disease or one or more symptoms associated with a vitamin B deficiency in a human patient in need thereof. The method comprises administering to a patient in need thereof, an aqueous solution comprising an effective amount of cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc, and optionally a chemical stabilizer and optionally a preservative, optionally a chemical stabilizer or a preservative, wherein the aqueous solution is formulated for intramuscular injection. In one embodiment, the method comprises administering to the patient an aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; wherein the composition is administered to the patient through subcutaneous/intradermal or intramuscular administration. In another embodiment, the method comprises administering to the patient an aqueous solution comprising about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4. In one embodiment, the composition is administered via intramuscular (IM) injection.

Provided herein is a method of treating or ameliorating a disease or one or more symptoms associated with a vitamin B deficiency in a human patient in need thereof. The method comprises administering to a patient in need thereof, an aqueous solution comprising an effective amount of cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), pantothenic acid (vitamin B5), and Zinc sulfate heptahydrate, and optionally a chemical stabilizer, preservative, or additional bioactive agent wherein the aqueous solution is formulated for intramuscular injection. In one embodiment, the method comprises administering to the patient an aqueous solution comprising between about 1500 to about 1500 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; wherein the composition is administered to the patient through subcutaneous, intradermal, intravenous, or intramuscular administration. In another embodiment, the method comprises administering to the patient an aqueous solution comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); about 10 mg pantothenic acid (vitamin B5); and about 0.1 mg Zinc sulfate heptahydrate, where the pH has been adjusted to about 7.4. In one embodiment, the composition is administered via injection.

Typically, symptoms of vitamin B deficiency include, but are not limited to, depression, dementia, fibrobromyalgia, gastrointestinal disorder, headaches, chronic fatigue syndrome, high stress levels, hyperthyroidism, low energy and impaired memory.

The methods described herein include methods for the treatment of disorders associated with vitamin B deficiencies. In some embodiments, the disorder is beriberi, Wernicke's encephalophay, ariboflavinosis, pellagra, acne, paresthesia, microcyrtic anemia, or macrocytic anemia.

In one aspect, a formulation is administered until one or more symptoms are reduced. In one embodiment, one or more symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Provided herein is a method of treating or improving one or more aspects of skin damage in a patient in need thereof comprising administering to the patient a composition described herein. In one embodiment, the composition is administered via intramuscular (IM) injection. In one embodiment, the composition is administered via other types of injection. For example, administration of a composition herein may improve skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent, or a combination thereof. In one embodiment, the method comprises administering to the patient an aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; wherein the composition is administered to the patient through intramuscular administration. In another embodiment, the method comprises administering to the patient an aqueous solution comprising about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4. In one embodiment, the method comprises administering to the patient an aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; wherein the composition is administered to the patient through injection. In another embodiment, the method comprises administering to the patient an aqueous solution comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); about 10 mg pantothenic acid (vitamin B5); and about 0.1 mg Zinc sulfate heptahydrate, where the pH has been adjusted to about 7.4.

In one aspect, a formulation is administered until one or more symptoms are improved. In one embodiment, skin elasticity, skin regeneration, metabolism, or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, metabolism, or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Also provided herein is a method of improving wound healing in a human patient in need thereof, comprising administering to the patient an aqueous solution composition described herein. In one embodiment, the composition is administered via subcutaneous/intradermal, via IV, via microneedle, or via intramuscular (IM) injection.

In one embodiment, the method comprises administering to the patient an aqueous solution comprising between about 500 to about 1500 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 2 to about 10 mg pyridoxine HCl (vitamin B6); between about 2 to about 10 mg riboflavin 5-phosphate sodium (vitamin B2); between about 0.5 to about 1.5 mg zinc; wherein the composition is administered to the patient through intramuscular administration. In one embodiment, a composition may be administered prior to surgery, after surgery, or both. Surgery may be, for example, plastic surgery or reconstructive surgery. In another embodiment, the method comprises administering to the patient an aqueous solution comprising about 1000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 1 mg zinc, where the pH has been adjusted to about 7.4. In some instances, the wound is a post-surgical wound or the result of trauma or surgery. In one embodiment, surgery is plastic surgery or reconstructive surgery. The treating physician may determine that the solution is to be administered prior to surgery, after surgery, or both. According to the method, the aqueous solution may be administered intramuscularly to a human on a daily basis, a weekly basis or as recommended depending on the judgment of the treating physician and the requirements of the individual patient.

In one embodiment, the method comprises administering to the patient an aqueous solution comprising between about 1500 to about 6250 mcg cobalamin (vitamin B12); between about 150 to about 250 mg ascorbic acid (vitamin C); between about 30 to about 50 mg nicotinamide (vitamin B3); between about 4.5 to about 7.5 mg thiamine (vitamin B1); between about 0.1 to about 0.3 mg pyridoxine HCl (vitamin B6); between about 2.7 to about 4.5 mg riboflavin 5-phosphate sodium (vitamin B2); between about 7.5 to 15 mg pantothenic acid (vitamin B5); and between about 0.08 to about 0.125 mg Zinc sulfate heptahydrate; wherein the composition is administered to the patient through injection. In one embodiment, a composition may be administered prior to surgery, after surgery, or both. Surgery may be, for example, plastic surgery or reconstructive surgery. In another embodiment, the method comprises administering to the patient an aqueous solution comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 0.1 mg pyridoxine hydrochloride (vitamin B6); about 3.6 mg riboflavin 5-phosphate sodium (vitamin B2); about 10 mg pantothenic acid (vitamin B5); and about 0.1 mg Zinc sulfate heptahydrate, where the pH has been adjusted to about 7.4. In some instances, the wound is a post-surgical wound or the result of trauma or surgery. In one embodiment, surgery is plastic surgery or reconstructive surgery. The treating physician may determine that the solution is to be administered prior to surgery, after surgery, or both. According to the method, the aqueous solution may be injected to a human on a daily basis, a weekly basis or as recommended depending on the judgment of the treating physician and the requirements of the individual patient.

Provided herein is a method of treating or improving one or more aspects of aging-related skin damage in a patient in need thereof comprising administering to the patient a composition described herein. In one embodiment, the composition is administered via intradermal injection. In another embodiment, the composition is administered via topical use. For example, administration of a composition herein may improve skin elasticity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, or a combination thereof.

In one embodiment for intradermal injection, the method comprises administering to the patient an aqueous solution comprising between about 4000 to about 5000 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 0.1 to about 0.2 mg pyridoxine HCl (vitamin B6); between about 2 to about 10 mg riboflavin 5-phosphate sodium (vitamin B2); between about 0.1 to about 0.2 mg zinc sulfate heptahydrate; between about 2.4 to 2.4 mg/ml HA. In another embodiment for topical use, the composition is administered via topical use, the method comprises administering to the patient an aqueous solution comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 0.1 mg zinc sulfate heptahydrate; and about 12 mg/ml HA, where the pH has been adjusted to about 7.4.

Zinc sulfate heptahydrate may be included in a composition that is formulated to improve provides aesthetic enhancement to a subject. In one embodiment, the aqueous solution comprises from about 0.05 to about 5 mg zinc sulfate heptahydrate, from about 0.75 to about 2 mg zinc sulfate heptahydrate, from about 0.1 to about 1 mg zinc sulfate heptahydrate, or from about 0.1 to about 0.5 mg zinc sulfate heptahydrate. In one embodiment, zinc sulfate heptahydrate is present in a composition in an amount of about 0.1 mg.

Hyaluronic acid may be included in a composition that is formulated to improve provides aesthetic enhancement to a subject. In one embodiment, the aqueous solution comprises from about 0.5 to about 25 mg/ml hyaluronic acid, from about 1.0 to about 20 mg/ml hyaluronic acid, from about 1.5 to about 15 mg/ml hyaluronic acid, or from about 2.4 to about 12 mg/ml hyaluronic acid. In one embodiment, hyaluronic acid is present in a composition in an amount of about 12 mg/ml.

In one aspect, a formulation is administered until one or more symptoms are improved. In one embodiment, skin elasticity, skin regeneration, skin hydration, skin luminosity, skin clarity or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, skin hydration, skin luminosity, skin clarity or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

An "effective amount" is an amount sufficient to result in one or more beneficial or desired results, either partially or completely. For example, a therapeutic amount is one that achieves the desired therapeutic effect. For example, a patient may experience about a 10%, 20%, 30%, 40%, 50%, 60%, 70%, 80%, 90%, or 100% improvement in one or more symptoms. This amount can be the same or different from a prophylactically effective amount, which is an amount necessary to improve aging-related skin conditions.

An effective amount can be administered in one or more administrations, applications or dosages. A therapeutically effective amount of a therapeutic compound (i.e., an effective dosage) depends on the aesthetic and therapeutic compounds selected.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered intradermally or topically to a patient on a daily basis, a weekly basis or as recommended depending on the judgment of the treating physician and the requirements of the individual patient. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

In one embodiment, a composition described herein is administered 1 day, 2 days, 3 days, 4 days, 5 days or 6 days prior to surgery. In another embodiment, a composition described herein is administered 1 day, 2 days, 3 days, 4 days, 5 days or 6 days after surgery. In yet another embodiment, a composition described herein is administered 1 day, 2 days, 3 days, 4 days, 5 days or 6 days prior to surgery and also 1 day, 2 days, 3 days, 4 days, 5 days or 6 days after surgery.

An "effective amount" is an amount sufficient to result in one or more beneficial or desired results, either partially or completely. For example, a therapeutic amount is one that achieves the desired therapeutic effect. For example, a patient may experience about a 10%, 20%, 30%, 40%, 50%, 60%, 70%, 80%, 90%, or 100% improvement in one or more symptoms. This amount can be the same or different from a prophylactically effective amount, which is an amount necessary to prevent onset of disease or disease symptoms.

An effective amount can be administered in one or more administrations, applications or dosages. A therapeutically effective amount of a therapeutic compound (i.e., an effective dosage) depends on the therapeutic compounds selected.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered to a patient on a daily basis, a weekly basis or as recommended depending on the judgment of the treating physician and the requirements of the individual patient. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

It may be appreciated that certain factors may influence the dosage and timing required to effectively treat a subject, including but not limited to the severity of the disease or disorder, previous treatments, the general health and/or age of the subject, and other diseases present.

Provided herein is a method of treating or improving one or more aspects of aging-related skin damage in a patient in need thereof comprising administering to the patient a composition described herein. In one embodiment, the composition is administered via intradermal injection. In another embodiment, the composition is administered via topical use. For example, administration of a composition herein may improve skin elasticity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, or a combination thereof. In one embodiment for intradermal injection, the method comprises administering to the patient an aqueous solution comprising between about 4000 to about 5000 mcg cobalamin (vitamin B12); between about 100 to about 200 mg ascorbic acid (vitamin C); between about 10 to about 60 mg nicotinamide (vitamin B3); between about 2 to about 10 mg thiamine (vitamin B1); between about 0.1 to about 0.2 mg pyridoxine HCl (vitamin B6); between about 2 to about 10 mg riboflavin 5-phosphate sodium (vitamin B2); between about 0.1 to about 0.2 mg zinc sulfate heptahydrate; between about 2.4 to 2.4 mg/ml HA and any concentration of collagen, botulinum toxin, platelet-rich plasma, and/or poly-L-lactic acid as determined necessary to achieve the aesthetic goals set by the doctor and patient. In another embodiment for topical use, the composition is administered via topical use, the method comprises administering to the patient an aqueous solution comprising about 5000 mcg cobalamin (vitamin B12); about 200 mg ascorbic acid (vitamin C); about 40 mg nicotinamide (vitamin B3); about 6 mg thiamine hydrochloride (vitamin B1); about 3 mg pyridoxine hydrochloride (vitamin B6); about 3.6 mg riboflavin 5-phosphate sodium (vitamin B2); and about 0.1 mg zinc sulfate heptahydrate; about 12 mg/ml HA, and any concentration of collagen, botulinum toxin, platelet-rich plasma, and/or poly-L-lactic acid where the pH has been adjusted to about 7.4.

In one aspect, a formulation is administered until one or more symptoms are improved. In one embodiment, skin elasticity, skin regeneration, skin hydration, skin luminosity, skin clarity or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, skin hydration, skin luminosity, skin clarity or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered intramuscularly, subcutaneously, intradermally, or topically to a patient on a daily basis, a weekly basis or as recommended depending on the judgment of the treating physician and the requirements of the individual patient. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

Microneedle Arrays

A microneedle array may contain between 1 and about 500 microneedles, which will be anywhere between about 0.1 and about 2.5 mm in length and between about 0.01 and about 0.5 mm in diameter, and be composed of any metal, metal alloy, metalloid, polymer, or combination thereof, such as gold, steel, silicon, PVP (polyvinylpyrrlidone) (Sullivan S P, Murthy N, Prausnitz M R: Minimally invasive protein delivery with rapidly dissolving polymer microneedles. *Adv Mat.* 2008 March; 20(5):933-938. PubMed PMCID: PMC3519393), etc. The microneedles may each have one or more recesses running a certain depth into the outer wall to allow for flow of the substance to be delivered down the microneedle and into the dermis; these recesses can be in a plurality of shapes, including but not limited to: straight line, cross shape (+), flat shape (−), or screw thread shape going clockwise or counterclockwise (see, US Publication Number: US 2012-0296280 A1).

The array may be in any shape or combination of shapes, continuous, or discontinuous. The list of possible shapes includes, but is not limited to, circles, triangles, rectangles, squares, rhomboids, trapezoids, and any other regular or irregular polygons.

The array may be attached to a reservoir to hold the substances to be delivered, and this reservoir may be any volume (about 0.25 mL to about 5 mL), shape, color, or material (glass, metal, alloy, or polymer), as determined necessary.

This reservoir will itself be attached to or contain a means to encourage flow of the drug solutions contained in the reservoir into the skin. Two non-limiting examples of such means are 1) a plate and spring that allows the contained solutions to flow only when the device is tapped into the skin, and 2) a syringe that contains the drug solutions to be delivered and includes a plunger that can be depressed to mechanically drive the solution into the skin.

Delivered substances may be in any concentration, e.g., from about 0.01% to about 100%, and will be administered via a microneedle array either independently, or in conjunction with the aforementioned bioactive formulations. The formulations that may be administered using such microneedle arrays include any of the solutions (formulations) described herein. The aforementioned components of the solutions may be combined in any ratio, and administered in any volume, as determined necessary.

The device may improve the health and vitality of the skin, as described above. This may be achieved both by the delivery of bioactive formulations directly to the dermis and by the mechanical stimulation of the nerve endings in the skin from the tapping of the microneedle device onto the surface of skin.

While the uses of the microneedle injection as a general delivery method have been previously explored, the use of a method to deliver certain bioactive skin-enhancing substances or compositions described herein to the skin itself more efficiently have not been. The coupling of this delivery method with any of the substances listed above to improve skin health has significant potential.

Improved skin health, as used above, includes but is not limited to improved appearance, increased regeneration, increased elasticity, increased anti-oxidative level, reduced photo-aging, reduced wrinkles, reduced scarring, reduced bacterial activities including acne, redistribution of fat and/or other content of the skin, reduced number and/or sizes of pores, reduced callusing, reduced sweating and/or body odor through skin, improved scalp health, increased hair density, increased evenness of hair growth, and increased hair strength.

One would understand that a microneedle array as described herein may be used to administer any of the compositions described herein to a subject in need thereof.

EXAMPLES

The application may be better understood by reference to the following non-limiting examples, which are provided as exemplary embodiments of the application. The following examples are presented in order to more fully illustrate exemplary embodiments and should in no way be construed, however, as limiting the broad scope of the application.

Example 1

An aqueous solution containing the following ingredients:
about 500 to about 1500 mcg cobalamin (vitamin B12);
about 100 to about 200 mg ascorbic acid (vitamin C);
about 10 to about 60 mg nicotinamide (vitamin B3);
about 2 to about 10 mg thiamine (vitamin B1);
about 2 to about 10 mg pyridoxine HCl (vitamin B6);
about 2 to about 10 mg riboflavin 5-phosphate sodium (vitamin B2);
about 0.5 to about 1.5 mg zinc
about 1 ml q.s., sterile water for injection The aqueous solution is formulated in physiological saline and adjusted an acceptable pH in the range of about 6.5 to about 7.5 to 7.4, thereby minimizing any injecting pain beyond the needle prick. The aqueous solution may be optionally supplemented with a preservative (e.g., from about 0.01% to about 2% benzyl alcohol) and/or a chemical stabilizer (e.g., from about 0.01% to about 2% gentisic acid), depending on anticipated shelf-life.

Example 2

This example provides a representative example of an aqueous solution to be used in a method described herein. The composition may contain the following ingredients:

| | |
|---|---|
| 1000 mcg | cobalamin (vitamin B12) |
| 200 mg | ascorbic acid (vitamin C) |
| 40 mg | nicotinamide (vitamin B3) |
| 6 mg | thiamine (vitamin B1) |
| 6 mg | pyridoxine HCl (vitamin B6) |
| 3.6 mg | riboflavin 5-phosphate sodium (vitamin B2) |
| 1 mg | zinc |
| 1 ml | q.s., sterile water for injection |

The aqueous solution is formulated in physiological saline and adjusted to about pH 7.4, thereby minimizing any injecting pain beyond the needle prick. In addition, the aqueous solution may be optionally supplemented with a preservative (e.g., benzyl alcohol) and/or a chemical stabilizer (e.g., gentisic acid), depending on anticipated shelf-life.

Example 3

The purpose of this example is to evaluate the efficacy of a composition described herein in treating the signs of aging present on facial skin. A composition is prepared as in Example 2.

Two groups of human subjects (8-10 subjects per group) are injected intramuscularly with the composition or physiological saline (control) twice a day for a period of 29 days. At the end of the 29 day test period, the subjects are polled regarding various aspects of the effectiveness of the composition described herein in treating and/or minimizing signs of aging present on the skin. The following aspects of the composition described herein are evaluated:

(1) effectiveness of the composition described herein in improving the smoothness and/or softness of skin (i.e., making the skin feel smoother and softer following treatment);

(2) effectiveness of the composition described herein in improving the overall appearance of skin;

(3) effectiveness of the composition described herein in evening out skin tone and texture;

(4) effectiveness of the composition described herein in improving the clarity and/or radiance of skin;

(5) effectiveness of the composition described herein in making the skin look younger; and (6) effectiveness of the composition described herein in making wrinkles appear softer and/or less prominent.

Patients treated with the composition exhibit improvement in one or more of the symptoms described herein.

Example 4

The purpose of this example is to evaluate the efficacy of a composition described herein in treating the signs of aging present on facial skin. A composition is prepared as in Example 2.

Two groups of human subjects (8-10 subjects per group) are injected intramuscularly with the composition or physiological saline (control) on days 1, 3, 7, 10, 14, 21, 30, 60, and 90 of treatment. At the end of the 90-day test period, the subjects are polled regarding various aspects of the effectiveness of the composition described herein in treating and/or minimizing signs of aging present on the skin. The following aspects of the composition described herein are evaluated:

(1) effectiveness of the composition described herein in improving the smoothness and/or softness of skin (i.e., making the skin feel smoother and softer following treatment);

(2) effectiveness of the composition described herein in improving the overall appearance of skin;

(3) effectiveness of the composition described herein in evening out skin tone and texture;

(4) effectiveness of the composition described herein in improving the clarity and/or radiance of skin;

(5) effectiveness of the composition described herein in making the skin look younger; and (6) effectiveness of the composition described herein in making wrinkles appear softer and/or less prominent.

Patients treated with the composition exhibit improvement in one or more of the symptoms described herein.

Example 5

An aqueous solution containing the following ingredients:
about 1500 to about 6250 mcg cobalamin (vitamin B12);
about 150 to about 250 mg ascorbic acid (vitamin C);
about 30 to about 50 mg nicotinamide (vitamin B3);
about 4.5 to about 7.5 mg thiamine (vitamin B1);
about 0.1 to about 0.3 mg pyridoxine HCl (vitamin B6);
about 2.7 to about 4.5 mg riboflavin 5-phosphate sodium (vitamin B2);
about 7.5 to about 15 mg pantothenic acid (vitamin B5);
about 0.08 to about 0.125 mg Zinc sulfate heptahydrate; and
about 1 ml q.s., sterile water for injection The aqueous solution is formulated in physiological saline and adjusted an acceptable pH in the range of about 6.5 to about 7.5 to 7.4, thereby minimizing any injecting pain beyond the needle prick. The aqueous solution may be optionally supplemented with a preservative (e.g., from about 0.01% to about 2% benzyl alcohol), a chemical stabilizer (e.g., from about 0.01% to about 2% gentisic acid), and/or an additional bioactive agent (e.g., from about 0.01% to about 2% hyaluronic acid) depending on anticipated delivery method, shelf-life, and intended effects.

Example 6

This example provides a representative example of an aqueous solution to be used in a method described herein. The composition may contain the following ingredients:

| | |
|---|---|
| 5000 mcg | cobalamin (vitamin B12) |
| 200 mg | ascorbic acid (vitamin C) |
| 40 mg | nicotinamide (vitamin B3) |
| 6 mg | thiamine (vitamin B1) |
| 6 mg | pyridoxine HCl (vitamin B6) |
| 3.6 mg | riboflavin 5-phosphate sodium (vitamin B2) |
| 10 mg | pantothenic acid (vitamin B5) |
| 0.1 mg | Zinc sulfate heptahydrate |
| 1 ml | q.s., sterile water for injection |

The aqueous solution is formulated in physiological saline and adjusted to about pH 7.4, thereby minimizing any injecting pain beyond the needle prick. In addition, the aqueous solution may be optionally supplemented with a preservative (e.g., benzyl alcohol), a chemical stabilizer (e.g., gentisic acid), and/or an additional bioactive agent (e.g., platelet-rich plasma) depending on anticipated delivery method, shelf-life, and intended effects.

Example 7

The purpose of this example is to evaluate the efficacy of a composition described herein in treating the signs of aging present on facial skin. A composition is prepared as in Example 6.

Two groups of human subjects (8-10 subjects per group) are injected with the composition or physiological saline (control) twice a day for a period of 29 days. At the end of the 29 day test period, the subjects are polled regarding various aspects of the effectiveness of the composition described herein in treating and/or minimizing signs of aging present on the skin. The following aspects of the composition described herein are evaluated:

(1) effectiveness of the composition described herein in improving the smoothness and/or softness of skin (i.e., making the skin feel smoother and softer following treatment);

(2) effectiveness of the composition described herein in improving the overall appearance of skin;

(3) effectiveness of the composition described herein in evening out skin tone and texture;

(4) effectiveness of the composition described herein in improving the clarity and/or radiance of skin;

(5) effectiveness of the composition described herein in making the skin look younger; and (6) effectiveness of the composition described herein in making wrinkles appear softer and/or less prominent.

(7) effectiveness of the composition described herein in increasing the degree of hydration of the skin.

Patients treated with the composition exhibit improvement in one or more of the symptoms described herein.

Example 8

The purpose of this example is to evaluate the efficacy of a composition described herein in treating the signs of aging present on facial skin. A composition is prepared as in Example 6.

Two groups of human subjects (8-10 subjects per group) are injected with the composition or physiological saline (control) on days 1, 3, 7, 10, 14, 21, 30, 60, and 90 of treatment. At the end of the 90-day test period, the subjects are polled regarding various aspects of the effectiveness of the composition described herein in treating and/or minimizing signs of aging present on the skin. The following aspects of the composition described herein are evaluated:

(1) effectiveness of the composition described herein in improving the smoothness and/or softness of skin (i.e., making the skin feel smoother and softer following treatment);

(2) effectiveness of the composition described herein in improving the overall appearance of skin;

(3) effectiveness of the composition described herein in evening out skin tone and texture;

(4) effectiveness of the composition described herein in improving the clarity and/or radiance of skin;

(5) effectiveness of the composition described herein in making the skin look younger; and (6) effectiveness of the composition described herein in making wrinkles appear softer and/or less prominent.

(7) effectiveness of the composition described herein in increasing the degree of hydration of the skin.

Patients treated with the composition exhibit improvement in one or more of the symptoms described herein.

While preferred embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments described herein may be employed. It is intended that the following claims define the scope of the embodiments and that methods and structures within the scope of these claims and their equivalents be covered thereby.

REFERENCES

1. Papakonstantinou, E., Roth, M. & Karakiulakis, G. Hyaluronic acid: A key molecule in skin aging. *Dermato-endocrinology* 4, 253-258, doi:10.4161/derm.21923 (2012).
2. Fagien, S. & Cassuto, D. Reconstituted injectable hyaluronic acid: expanded applications in facial aesthetics and additional thoughts on the mechanism of action in cosmetic medicine. *Plastic and reconstructive surgery* 130, 208-217, doi:10.1097/PRS.0b013e318254b3f6 (2012).
Varani J, Dame M K, Rittie L, Fligiel S E G, Kang S, Fisher G J, Voorhees J J: Decreased Collagen Production in Chronically Aged Skin. Am J Pathol. 2006 June; 168(6): 1861-1868. PubMed PMCID: PMC1606623.
BOTOX (onabotulinumtoxinA) [prescribing information]. Irvine, Calif. Allergan, Inc. January 2013.
Borrione P, Gianfrancesco A D, Pereira M T, Pigozzi F: Platelet-rich plasma in muscle healing. Am J Phys Med Rehabil. 2010 October; 89(10):854-61. PubMed PMID: 20855985.
SCULPTRA Aesthetic (injectable poly-L-lactic acid) [prescribing information]. Bridgewater, N.J. Sanofi-Aventis U.S. LLC. May 2012.

What is claimed is:

1. An aqueous solution formulated for subcutaneous, intradermal or intramuscular injection in a human subject, comprising:

from about 1500 to about 6250 mcg cobalamin (vitamin B12);

from about 150 to about 250 mg ascorbic acid (vitamin C);

from about 30 to about 50 mg nicotinamide (vitamin B3);

from about 4.5 to about 7.5 mg thiamine (vitamin B1);

from about 0.1 to about 0.3 mg pyridoxine HCl (vitamin B6);

from about 2.7 to about 4.5 mg riboflavin 5-phosphate sodium (vitamin B2);

from about 7.5 to about 15 mg pantothenic acid (vitamin B5); and from about 0.08 to about 0.125 mg Zinc sulfate heptahydrate;

wherein the aqueous solution has a volume not exceeding 2 ml, wherein the solution improves skin condition, enhances skin texture, appearance, or a combination thereof upon subcutaneous, intradermal or intramuscular injection.

2. The solution of claim 1, wherein the solution comprises:

5000 mcg cobalamin (vitamin B12);
200 mg ascorbic acid (vitamin C);
40 mg nicotinamide (vitamin B3);
6 mg thiamine (vitamin B1);
0.1 mg pyridoxine HCl (vitamin B6);
3.6 mg riboflavin 5-phosphate sodium (vitamin B2);
10 mg pantothenic acid (vitamin B5); and
0.1 mg Zinc sulfate heptahydrate.

3. The solution of claim 1, wherein the solution comprises a chemical stabilizer, wherein the chemical stabilizer is gentisic acid.

4. The solution of claim 1, wherein the solution comprises a preservative, wherein the preservative is benzyl alcohol.

5. The solution of claim 1, wherein the solution comprises an additional bioactive agent, wherein the additional bioactive agent is hyaluronic acid, botulinum toxin, platelet-rich plasma, or polylactic acid.

6. The solution of claim 1, wherein the solution has a pH between about 7.2 and 7.6.

7. The solution of claim 6, wherein the solution has a pH of 7.4.

8. The solution of claim 1, wherein the cobalamin is selected from the group consisting of cyanocobalamin and methylcobalamin.

9. The solution of claim 1, wherein the solution comprises a chemical stabilizer, a preservative and an additional bioactive agent.

10. The solution of claim 1, wherein the solution comprises a chemical stabilizer.

11. The solution of claim 1, wherein the solution comprises a preservative.

12. The solution of claim 1, wherein the solution comprises an additional bioactive agent.

13. The solution of claim 1, wherein the solution comprises two of a chemical stabilizer, a preservative and an additional bioactive agent.

14. The composition of claim 1, wherein the solution is formulated for subcutaneous injection.

15. The composition of claim 1, wherein the solution is formulated for intradermal injection.

16. The composition of claim 1, wherein the solution is formulated for intramuscular injection.

17. An aqueous solution formulated for subcutaneous, intradermal or intramuscular injection in a human subject, comprising:

from about 1500 to about 6250 mcg cobalamin (vitamin B12);

from about 150 to about 250 mg ascorbic acid (vitamin C);

from about 30 to about 50 mg nicotinamide (vitamin B3);

from about 4.5 to about 7.5 mg thiamine (vitamin B1);

from about 0.1 to about 0.3 mg pyridoxine HCl (vitamin B6);

from about 2.7 to about 4.5 mg riboflavin 5-phosphate sodium (vitamin B2);

from about 7.5 to about 15 mg pantothenic acid (vitamin B5); and from about 0.08 to about 0.125 mg Zinc sulfate heptahydrate;

wherein the aqueous solution has a volume up to about 5.0 ml, wherein the solution improves skin condition, enhances skin texture, appearance, or a combination thereof upon subcutaneous, intradermal or intramuscular injection.

* * * * *